(12) United States Patent
Bhutia et al.

(10) Patent No.: US 11,732,200 B2
(45) Date of Patent: Aug. 22, 2023

(54) PROCESS FOR ENHANCEMENT OF RON OF FCC GASOLINE WITH SIMULTANEOUS REDUCTION IN BENZENE

(71) Applicant: Indian Oil Corporation Limited, Mumbai (IN)

(72) Inventors: Sandup Tshering Bhutia, Faridabad (IN); Vineeth Venu Nath, Faridabad (IN); Arvind Wamandas Mahant, Faridabad (IN); Bandaru Hari Venkata Prasad Gupta, Faridabad (IN); Ram Mohan Thakur, Faridabad (IN); Madhusudan Sau, Faridabad (IN); Gurpreet Singh Kapur, Faridabad (IN); Sankara Sri Venkata Ramakumar, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 0 days.

(21) Appl. No.: 17/656,445

(22) Filed: Mar. 25, 2022

(65) Prior Publication Data
US 2022/0306946 A1 Sep. 29, 2022

(30) Foreign Application Priority Data
Mar. 25, 2021 (IN) .............................. 202121013132

(51) Int. Cl.
*C10G 35/06* (2006.01)
*C10G 35/095* (2006.01)
*C07C 2/66* (2006.01)

(52) U.S. Cl.
CPC ............. *C10G 35/065* (2013.01); *C07C 2/66* (2013.01); *C10G 35/095* (2013.01); *C10G 2300/305* (2013.01)

(58) Field of Classification Search
CPC ................ C10G 35/065; C10G 35/095; C10G 2300/305; C10G 2300/701;
(Continued)

(56) References Cited

U.S. PATENT DOCUMENTS 4,012,455 A * 3/1977 Owen ....................... C10G 3/49
585/407
4,140,622 A 2/1979 Herout et al.
(Continued)

FOREIGN PATENT DOCUMENTS

CA 2951614 A1 2/2017
CN 101508906 A 8/2009
(Continued)

OTHER PUBLICATIONS

Eman Ali Eh. Sheet & Nabil Majd Alawi "Process for producing high octane gasoline having lower benzene content and distillation end point with its environmental effect of engine exhaust emissions" Petroleum Chemistry vol. 54, pp. 157-164 (Mar. 18, 2014).

*Primary Examiner* — Ali Z Fadhel
(74) *Attorney, Agent, or Firm* — Workman Nydegger

(57) ABSTRACT

The present invention relates to an integrated process for increasing the research octane number (RON) of FCC gasoline with simultaneous reduction in benzene content. In this process, benzene rich gasoline fraction is reacted with light olefin rich gaseous streams like FCC off gas/dry gas, coker off gas to produce alkyl aromatics using FCC catalyst system containing ZSM-5 zeolite. The catalyst is continuously drawn from the FCC regenerator by suitably placing the alkylation reactor in communication with the FCC regenerator. The product stream of the alkylation reactor is routed to main fractionator for separation of off gas and benzene lean gasoline. This integrated process not only improves the octane number of gasoline but also lowers the gasoline benzene content. Further the integrated alkylation (Continued)

reactor system acts as a heat sink lowering the FCC regenerator temperature and enables the FCC unit to process high CCR feeds.

10 Claims, 1 Drawing Sheet

(58) Field of Classification Search
CPC .. C10G 2400/02; C10G 11/18; C10G 29/205; C07C 2/66; B01J 29/084; B01J 29/40; B01J 29/80
See application file for complete search history.

(56) References Cited

U.S. PATENT DOCUMENTS

| | | | |
|---|---|---|---|
| 4,992,607 A * | 2/1991 | Harandi | C07C 2/66 585/323 |
| 5,041,208 A | 8/1991 | Patridge et al. | |
| 5,149,894 A | 9/1992 | Holtermann et al. | |
| 5,252,197 A * | 10/1993 | Alexander | C10G 35/095 585/475 |
| 5,347,061 A | 9/1994 | Harandi et al. | |
| 5,481,057 A * | 1/1996 | Bell | C10G 57/005 585/314 |
| 5,491,270 A * | 2/1996 | Chin | C10G 29/205 585/446 |
| 7,029,571 B1 * | 4/2006 | Bhattacharyya | C10G 11/18 208/77 |
| 8,889,937 B2 * | 11/2014 | Haizmann | C07C 6/123 585/446 |
| 2004/0171899 A1 | 9/2004 | Pohl | |
| 2009/0112028 A1 * | 4/2009 | Schultz | C07C 2/66 585/314 |
| 2011/0240519 A1 | 10/2011 | Jan et al. | |
| 2011/0305602 A1 * | 12/2011 | Nicholas | C10G 11/18 422/142 |
| 2014/0014555 A1 * | 1/2014 | Marri | C10G 51/026 208/78 |
| 2014/0194660 A1 * | 7/2014 | Hwang | C10G 29/205 585/449 |
| 2015/0274613 A1 * | 10/2015 | Pham | C10G 11/18 585/324 |
| 2022/0228073 A1 * | 7/2022 | Koseoglu | C10G 11/18 |

FOREIGN PATENT DOCUMENTS

| | | |
|---|---|---|
| WO | 2010104581 A2 | 9/2010 |
| WO | 2011156182 A2 | 12/2011 |

* cited by examiner

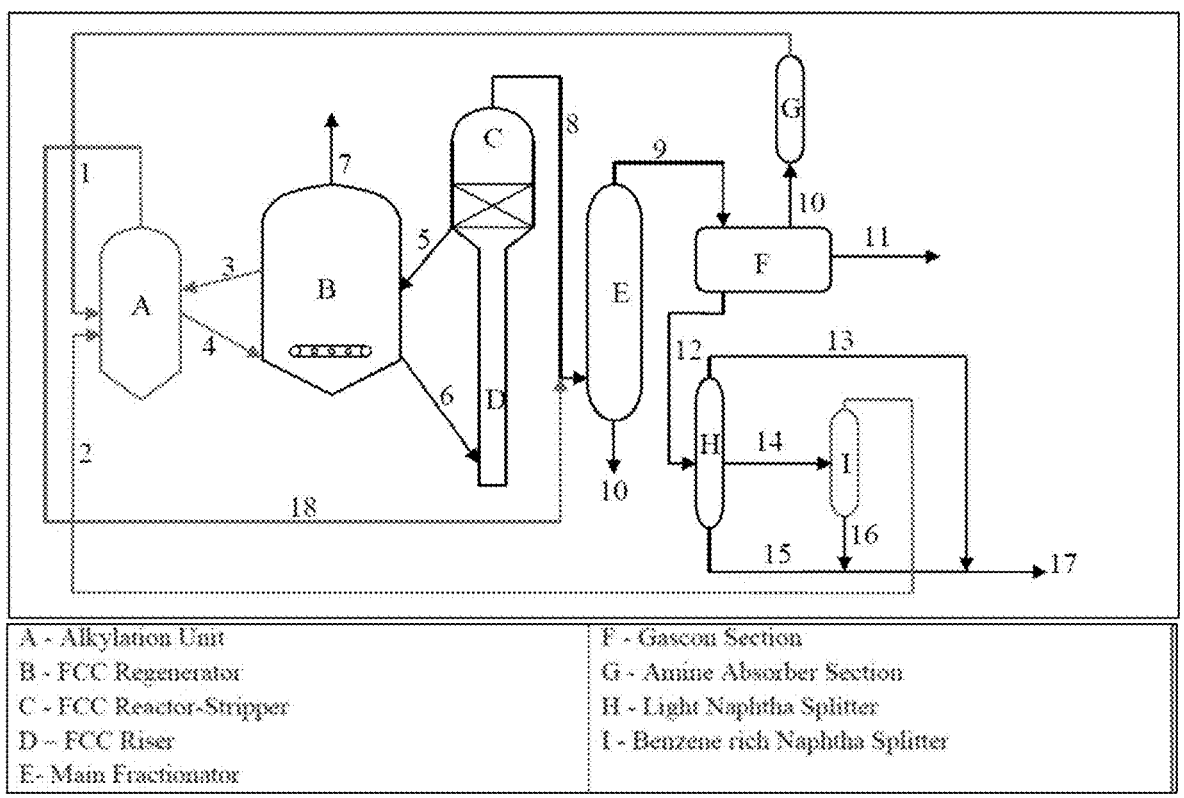

PROCESS FOR ENHANCEMENT OF RON OF FCC GASOLINE WITH SIMULTANEOUS REDUCTION IN BENZENE

FIELD OF THE INVENTION

The present invention relates to an integrated process for increasing the research octane number (RON) of FCC gasoline with simultaneous reduction in benzene content wherein benzene rich gasoline fraction is reacted with light olefin rich gaseous streams like FCC off gas/dry gas, coker off gas in presence of FCC catalyst system containing ZSM-5 zeolite.

BACKGROUND OF THE INVENTION

Benzene is present in gasoline because of its natural occurrence in crude oil. It is also generated during processing of crude oil such as catalytic cracking, catalytic reforming and lands into gasoline fraction. Benzene is recognized as a toxic chemical capable of causing serious health hazard and impact on environment. High severity FCC units produce large quantity of light olefins and aromatics resulting in higher benzene in FCC gasoline. Environmental regulations mandate benzene level in gasoline pool lower than 0.62 vol % with a maximum of 1.0 vol %. The removal of benzene represents a loss in gasoline volume as well as gasoline octane.

Various techniques are widely practiced for reducing benzene in gasoline. One such route is to selectively alkylate the benzene using light olefins in presence of shape-selective crystalline zeolites.

U.S. Pat. No. 5,149,894 describes a process for converting benzene to alkyl benzenes in a gasoline blend stock. The process involves contacting a benzene-containing gasoline blend stock with a C2-C4 olefin stream in the presence of a catalyst containing the zeolite, SSZ-25, to produce an alkylated light hydrocarbon stream with reduced benzene content.

U.S. Pat. No. 4,140,622 describes a process for alkylating benzene containing fraction with light hydrocarbon stream such as ethylene, propylene, butylenes or a mixture of light olefinic hydrocarbons with an alkylation catalyst comprising SPA (solid phosphoric acid).

U.S. Pat. No. 5,491,270 describes a process for alkylating benzene rich gasoline stream with $C_{5+}$ olefins to produce product gasoline having reduced benzene content in presence of acidic ZSM-5 catalyst without substantially increasing higher $C_{10+}$ alkyl aromatics.

US Patent Publication 2004/0171899 describes a process for producing an alkyl aromatic compound contacting a dilute olefin feed with a lean oil stream containing aromatic compound and alkyl aromatic compound. The dilute olefin feed is sent to an absorber and contacted with a chemical stream which absorbs most of the ethylene, separates hydrogen and other inert low molecular weight impurities, such as methane, ethane, nitrogen, carbon dioxide and carbon monoxide, and less commonly butane and pentane. The absorbed ethylene is sent to an alkylator where it is reacted with benzene. The alkylator is a fixed bed reactor containing catalyst such as Zeolite, for example, zeolite BEA (beta), zeolite MWW, Zeolite Y, Mordenite catalyst, MFI catalyst, Faujasite catalyst; or any other molecular Sieve catalyst suitable for liquid phase alkylation or combinations of any of the above catalysts. Zeolite BEA is preferred.

The present invention overcomes the drawback of prior arts, high benzene, and low RON of gasoline by integrating the alkylation reactor system with the FCC process.

OBJECTIVES OF THE PRESENT INVENTION

It is primary objective of the invention to enhance gasoline RON by integrating alkylation reactor system with the FCC process.

It is further objective of the present invention to provide simultaneous reduction of benzene in FCC gasoline. with increase in RON.

It is further objective of the present invention to provide an integrated Fluid Catalytic Cracking (FCC) and Alkylation process.

It is another objective of the present invention to provide a process for value addition of FCC off gas stream (dry gas) by converting into liquid fuel i.e., valorization of dry gas.

It is another objective of the present invention to lower FCC regenerator dense bed temperature thereby increasing the FCC unit conversion, wherein the integrated alkylation reactor functions as a catalyst cooler/heat sink.

SUMMARY OF THE PRESENT INVENTION

The present invention provides an integrated process for increasing the research octane number (RON) of gasoline and simultaneous reduction in benzene, said process comprises contacting benzene rich gasoline fraction with light olefin rich stream in a fluidized bed alkylation reactor with ZSM-5 containing FCC catalyst to produce alkyl aromatics. Catalyst is continuously drawn from the FCC regenerator, which is in communication with alkylation reactor, whereby stream from alkylation reactor is separated into off gas and benzene lean gasoline.

In one feature, the present invention utilizes a catalyst system comprising two components; wherein first component comprises of FCC catalyst containing Y-type Zeolite, an active alumina material, a binder material, comprising either silica or alumina or combination thereof and an inert filler such as kaolin, and the second component contains medium or smaller pore zeolite, preferably ZSM-5 based additive, wherein the ZSM-5 additive is preferably in the range of 5-50 wt % of the total catalyst system.

In another preferred feature of the present invention, the temperature of benzene rich gasoline fraction and light olefin rich gaseous streams is in range of 40-60° C. and 30-50° C., respectively.

In one feature of the present invention, light olefin rich stream is selected from group consisting of dilute ethylene stream, FCC off gas/dry gas, and coker off gas.

In another feature of the present invention, the benzene content is reduced by 30-50 weight percent relative to benzene rich gasoline fraction.

In another feature of the present invention, the benzene content is reduced by at least 40 weight percent relative to benzene rich gasoline fraction.

In another feature of the present invention, the yield of gasoline ranges from 81-95%.

In one feature of the present invention, the alkyl aromatics is alkyl benzene.

In one feature, the present invention provides a refinery complex system comprising of an FCC unit having a riser-reactor D, reactor C, regenerator B, fractionator E with a product recovery section, and an alkylation unit A.

In another preferred feature, the present invention provides a refinery complex system for increasing the research octane number (RON) of gasoline and simultaneous reduction in benzene, the system comprising:

a) FCC riser (D)
  to contact hydrocarbon streams with hot regenerated cracking catalyst, and cracking into lighter molecular weight hydrocarbon products;
b) FCC Regenerator (B)
  to combust the coke on catalyst, to produce regenerated catalyst and flue gas,
  to add substantial amount of heat to the catalyst, providing energy to offset the endothermic cracking reactions occurring in the riser-reactor (D),
  to provide continuous catalyst supply to alkylation reactor and regenerate the catalyst returning from the alkylation reactor;
c) Main Fractionator (E)
  to fractionate gaseous vapor into various cuts i.e., lighter components such as $H_2$, $C_1$-$C_4$ & light naphtha, and other liquid products such as heavy naphtha, light cycle oils, heavy cycle oils and slurry oils;
d) Gascon Section (F)
  to separate light naphtha and gaseous light hydrocarbons into dry gas stream and LPG stream;
e) Amine Absorber Section (G)
  to remove hydrogen sulfide from dry gas/dilute ethylene stream;
f) Light Naphtha Splitter (H)
  to separate the gasoline into three cuts namely light, medium and heavy cut;
g) Benzene rich Splitter (I)
  to fractionate medium cut into top cut and a bottom cut, to concentrate benzene into a separate stream;
h) Alkylation reactor/unit (A) integrated with the FCC regenerator (B)
  to contact hot regenerated catalyst with the dry gas containing dilute ethylene stream and benzene rich stream to produce alkyl aromatics,
  to continuously withdraw regenerated catalyst from the FCC regenerator and send back to regenerator after alkylation reaction.

In another feature of the present invention, the alkylation reactor temperature is in the range of 300-400° C.

In another feature of the present invention, the integrated alkylation reactor is useful as a catalyst cooler/heat sink and enables the FCC unit to process high CCR feeds.

In the present invention, the hydrocarbon stream (a) is selected from raw oil stream such as Vacuum gas oil (VGO) or hydrotreated VGO or reduced crude oil (RCO) or short residue (SR) or any other heavy or light hydrocarbon streams including naphtha or combination thereof.

Various objects, features, aspects, and advantages of the present invention will become more apparent from the following detailed description of preferred embodiments of the invention.

BRIEF DESCRIPTION OF DRAWINGS

FIG. 1: Scheme of integrated FCCU & Alkylation process for enhancement of RON of FCC gasoline with simultaneous reduction in benzene.

DETAILED DESCRIPTION OF THE INVENTION

The present invention provides an integrated Fluid Catalytic Cracking (FCC) and Alkylation process, wherein the dry gas containing light olefins is converted into alkyl aromatics by alkylation with a benzene-rich fraction, which is obtained by fractionating the FCC gasoline into a benzene rich cut.

In one embodiment of the present invention, other benzene streams are used, such as reformate stream from naphtha catalytic reformer unit.

In one embodiment of the present invention, hydrocarbon stream containing pure ethylene and a dilute proportion of ethylene is used. FCC dry gas stream is a suitable dilute ethylene stream.

In another embodiment of the present invention, other dilute ethylene streams such as coker dry gas streams are also utilized.

In a preferred embodiment, ethylene from an FCC dry gas stream is utilized.

In the present invention, in a riser (D), a heavy hydrocarbon feed or raw oil stream such as Vacuum gas oil (VGO) or hydrotreated VGO or reduced crude oil (RCO) or short residue (SR) or any other heavy or light hydrocarbon streams including naphtha or combination thereof is contacted with a hot regenerated cracking catalyst entering from a regenerated catalyst standpipe (6). The contacting occurs in riser (D), extending upwardly to the bottom of a reactor vessel C. Heat from the catalyst vaporizes the hydrocarbon feed, and is thereafter cracked to lighter molecular weight hydrocarbon products in presence of the catalyst as both are transferred through riser (D) into the reactor vessel (C).

During the cracking reactions, coke deposits on the catalyst surface which lowers the catalyst activity. The cracked hydrocarbon products separated from the coked catalyst using cyclonic separators, include a primary separator and one or two stages of cyclones in the reactor vessel (C). The gaseous products exit the reactor vessel (C) through a product outlet line (8) to the lower section of main fractionation column (E). The spent or coked catalyst falls into a stripping section at the bottom of the reactor (D) in which steam is injected to strip any residual hydrocarbon vapor. After the stripping operation, the coked catalyst is carried to the catalyst regenerator (B) through a spent catalyst standpipe (5). In the catalyst regenerator (B), a stream of oxygen containing gas, such as air, is introduced through an air distributor to uniformly combust the coke on catalyst. Coke combustion produces a regenerated catalyst and flue gas. The catalyst regeneration process adds a substantial amount of heat to the catalyst, providing energy to offset the endothermic cracking reactions occurring in the riser-reactor (D). The catalyst and flue gas inside the regenerator vessel is separated by a set of cyclones. Catalyst separated from flue gas dispenses through dip legs from cyclones, while hot flue gas exits the regenerator vessel (B) through flue gas outlet line (7).

Regenerated catalyst is carried back to the riser (D) through the regenerated catalyst standpipe (6). The product recovery begins with the main fractionator (E). The gaseous vapor entering the main fractionator (E) via the line (8) is fractionated into various cuts. The lighter components such as $H_2$, $C_1$-$C_4$ & light naphtha are removed as overhead product, while liquid products such as heavy naptha, light cycle oils, heavy cycle oils and slurry oils are separated at different locations in the main fractionator and are routed to other unit as required or sent for further treatment facilities before discharging as marketable products.

The light naphtha and gaseous light hydrocarbons (9) are routed to the gascon section (F). The gascon section (F) constitutes of the wet gas compressor, high pressure separator, de-ethanizer, de-butanizer, primary & secondary absorber column. These sections are in continuous communication with the main fractionator (E). In the gascon section (F) the gases get separated into (a) dry gas stream (10) comprising predominantly ethylene & other gases such as $H_2$, $CH_4$ and $C_2H_6$, (b) LPG stream (11) consisting of $C_3$ and $C_4$ hydrocarbons and (c) stabilized naphtha stream (12).

In an embodiment of the present invention, dry gas/dilute ethylene stream (10) is sent to an amine adsorption unit (G) for removal of hydrogen sulfide. Optionally hydrogen sulfide-lean, amine-treated dilute ethylene stream is water washed to remove residual amine carried over from the amine absorber (G) and also to reduce the concentration of ammonia and carbon dioxide in the dilute ethylene stream in line (1). The dilute ethylene stream can be further treated to remove carbon monoxide and ammonia using adsorbents. The dilute ethylene gas stream is carried in line (1) to the alkylation unit (A).

In one embodiment, de-butanized gasoline exiting the gascon section (G) via line (12) is routed further downstream to a gasoline splitter (H). The splitter column (H) separates the gasoline in broadly three cuts namely light cut having boiling range of 30 to 70° C., medium cut having boiling range of 70 to 110° C. and heavy cut having boiling range of 110 to 150° C. The light cut exiting the column (H) via line (13) does not contain much of the benzene and is routed to downstream for further processing or direct blending to the gasoline pool via line (17). The bottom-heavy cut (15) from the splitter column (H) substantially contains $C_{8+}$ hydrocarbons and is routed to downstream processing or blending via line (17). The medium cut (14) exiting the column (H) where most of the benzene is concentrated is routed to another splitter column (I) which further fractionates the medium cut into top cut having a boiling range of 70 to 100° C., more precisely 75 to 90° C. and a bottom cut 100+° C. fraction. The operation of the splitter column (I) ensures that much of the benzene is concentrated into a separate overhead stream.

In one embodiment, bottom cut of the splitter column (I) majorly containing $C_{6+}$ hydrocarbons can be routed via line (16) to the main gasoline product line stream (17) for further processing or blending. Line (2) feeds the benzene rich stream to the alkylation reactor (A) and line (1) feeds dilute ethylene stream to alkylation reactor (A).

In a preferred embodiment, alkylation reactor (A) is integrated with the FCC regenerator. The catalyst to the alkylation reactor (A) is continuously withdrawn from the FCC regenerator (B) via a standpipe (3).

In another preferred embodiment, FCC catalyst typically comprises two components. The first component includes any of the well-known catalysts that are used in the art of fluidized catalytic cracking, such as a Y-type Zeolite, an active alumina material, a binder material, comprising either silica or alumina or combination thereof and an inert filler such as kaolin. The second catalyst component comprises a catalyst-containing, medium or smaller pore zeolite catalyst exemplified by ZSM-5 in addition to Y-Zeolite based FCC catalyst. FCC catalyst system includes 5-50 wt % of ZSM-5 additive as a second component in addition to Y-Zeolite based FCC catalyst.

Most of FCC regenerators operate in the range of 650-750° C. The high regenerator temperatures are the source of heat to cat cracking reactions occurring in the FCC riser (D). The hot regenerated catalyst enters the alkylating reactor, contacts with the cold feed coming in the reactor via line (1) & (2) and leaves the reactor via the line (4) and catalyst returns back to the regenerator. The dry gas stream enters the alkylation reactor (A) via nozzles distributed along the circumference of the alkylation reactor (A). The dry gas stream entering the alkylation reactor (A) is in the temperature range of 30-50° C. The benzene rich stream also enters the alkylation reactor (A) via nozzles distributed along the circumference of the alkylation reactor (A). The benzene rich stream entering the reactor via line (2) is in the temperature range of 40-60° C. The feed nozzles are placed inside the reactor in such a way that proper mixing and contact of the two feed streams is provided. Another option for feed injection would be such that both the streams are simultaneously fed using a single line ensuring proper mixing of the two components. The mixed olefin and aromatic stream contact the turbulent bed of regenerated FCC catalyst entering via line (3). The vapor phase alkylation reaction typically occurs at a temperature range of 300-400° C. The partially deactivated catalyst flows through the line (4) to the regenerator (B) where it is regenerated by controlled contact with air or other regeneration gas at elevated temperatures to remove carbonaceous deposits. The catalyst entering the regenerator (B) from the alkylator (A) via line (4) can be stripped of entrained hydrocarbons by employing steam or any inert gas as fluidizing stream in the transfer line (4). The feed to catalyst ratio is so adjusted to bring the catalyst temperature to reaction temperature of 300-400° C. This can be achieved as the reactants entering the alkylating reactor (A) are in cold conditions. Alkylation reaction is exothermic, and the heat released from the reaction can be controlled by varying the feed preheat temperature or feed flow rate in a known manner. In the alkylation reactor (A), the dilute ethylene present in the line (1) reacts with the benzene containing stream in the line (2) and produces alkyl aromatic. The alkylation reactor is a fluidized bed reactor comprising a mixture of both large pore and small pore zeolite catalyst depending on the operational condition of the FCC unit. The product vapors generated in the alkylating reactor (A) is separated in cyclones housed at the top of the reactor and exits via the product line (18).

In another embodiment, the gaseous vapor in line (18) is cooled by indirect heat exchange and then passed into the separation section (F) or directly fed to the main fractionator (E) as shown in the diagram. The gasoline fraction exiting the FCC gascon is lower in benzene content and higher in RON.

Example 1

This example illustrates the alkylation performance of a typical FCC catalyst having ZSM-5 additive.

The experiments were conducted in a fixed-fluidized bed tubular reactor using 9-12 g catalyst at reaction temperature of 300-400° C., as measured by the thermocouple located in the catalyst bed. The feed used for the experiments was a benzene rich gasoline fraction of 70-90° C. (10 wt % benzene) cut and ethylene. Two experiments with different catalyst constituents, FCC CAT-1 & FCC CAT-2 were conducted. FCC CAT-1 is comprising of ZSM-5 additive having low zeolite content (10-15 wt %), while FCC CAT-2 has ZSM-5 additive with high zeolite content (30-50 wt %). The flow rate of ethylene was controlled using mass flow controller and gasoline fraction was injected using a pre-calibrated syringe pump. The product gases & liquid are separated by passing the reactor exit gases through a glass condenser placed in chiller bath kept at −10° C. The reaction was carried out for 5 minutes and the gas collected was analyzed in a Refinery Gas Analyzer. The liquid product was analyzed in a Detailed Hydrocarbon Analyzer for composition and determining RON.

Benzene reduction and RON increase were calculated using the formulae given below, and the obtained results are presented in Table 1.

$$\% \text{ Benzene Reduction} = \frac{\text{weight of benzene(in)} - \text{weight of benzene (out)}}{\text{weight of benzene (in)}} * 100$$

$$RON \text{ increase} = RON \text{ of liquid product} - RON \text{ of gasoline feed}(70-90° \text{ C.})$$

TABLE 1

Experimental Results

| | Attributes | | | |
|---|---|---|---|---|
| | FCC CAT-1 | | FCC CAT-2 | |
| Wt of catalyst, gms | 9 | 11 | 9 | 12 |
| Reaction Temperature ° C. | 400 | 400 | 400 | 400 |
| Time on stream, min | 5 | 5 | 5 | 5 |
| Bz/Et (mol/mol) | 0.16 | 0.16 | 0.16 | 0.16 |
| Benzene Reduction (wt %) | 40.84 | 41.85 | 46.19 | 49.88 |
| Delta RON (from DHA analysis) | 2.76 | 2.25 | 7.95 | 9.53 |
| % Liquid yield (gasoline basis) | 88.46 | 89.33 | 83.54 | 81.79 |

It can be seen that the benzene content of liquid has reduced through the process with a simultaneous increase in the RON.

Advantages of the Present Invention i. Simultaneous reduction of benzene in FCC gasoline with increase in RON,
ii. Value addition of FCC off gas stream by converting into liquid fuel,
iii. No separate catalyst system required as the fluidized bed alkylation reactor utilizes the same FCC catalyst from the regenerator to produce alkyl aromatics by integrating with FCC.
iv. Reduction in FCC regenerator dense bed temperature thereby increasing the FCC unit conversion. The integrated alkylation reactor functions as a catalyst cooler/heat sink.
v. No additional downstream facility is required for separation of reactor effluent as the process utilizes existing downstream facilities of the FCC unit for product separation saving capital cost.

We claim:

1. A process for increasing a research octane number (RON) and simultaneously reducing benzene content of a feed, the process comprising:
   integrating an alkylation reactor (A) with a fluid catalytic cracking (FCC) regenerator (B), wherein the integrating comprises:
   continuously withdrawing a hot regenerated catalyst from the FCC regenerator, wherein the FCC regenerator is configured to combust coke on a catalyst to generate the hot regenerated catalyst;
   contacting the hot regenerated catalyst with a stream comprising a light olefin and a stream having 10 wt % benzene to produce alkyl aromatics in the alkylation reactor; and
   sending back a spent catalyst to the FCC regenerator, wherein the catalyst comprises an FCC catalyst and 5-50 wt % of ZSM-5 additive.

2. The process as claimed in claim 1, wherein the FCC catalyst comprises Y-type Zeolite, an active alumina material, a binder material, and an inert filler, wherein the binder material comprises silica, alumina or a combination thereof, and wherein the inert filler comprises kaolin.

3. The process as claimed in claim 1, wherein the stream having benzene has a temperature in a range of 40-60° C., and wherein the stream comprising the light olefin has a temperature in a range of 30-50°.

4. The process as claimed in claim 1, wherein the stream comprising the light olefin is selected from the group consisting of a dilute ethylene stream, an FCC off gas/a dry gas, and a coker off gas.

5. The process as claimed in claim 1, wherein benzene content is reduced by 30-50 weight percent relative to the stream having benzene.

6. The process as claimed in claim 1, wherein the RON of the feed is increased by 2-10 units.

7. The process as claimed in claim 1, wherein the alkyl aromatics comprise alkyl benzene.

8. A refinery system for increasing a research octane number (RON) and for simultaneously reducing benzene content of a feed, the system comprising:
   an FCC riser (D), wherein the FCC riser is configured to contact hydrocarbon streams with a hot regenerated catalyst, and cracking the hydrocarbon streams into lighter molecular weight hydrocarbon products;
   an FCC Regenerator (B) configured to combust coke on a catalyst to produce a hot regenerated catalyst and a flue gas, and to add heat to the catalyst, providing energy to offset endothermic cracking reactions occurring in the FCC riser, wherein the catalyst comprises an FCC catalyst and 5-50 wt % of ZSM-5 additive;
   a Main Fractionator (E) configured to fractionate gaseous vapor into cuts comprising H2, C1-C4, and light naphtha, and liquid products comprising heavy naphtha, light cycle oils, heavy cycle oils and slurry oils;
   a Gascon Section (F) configured to separate the light naphtha and the gaseous vapor into a dry gas stream and an LPG stream;
   an Amine Absorber Section (G) configured to remove hydrogen sulfide from the dry gas stream;
   a Light Naphtha Splitter (H) configured to separate the light naphtha into three cuts, wherein the three cuts comprise a light cut, a medium cut and a heavy cut;
   a Benzene rich Splitter (I) configured to fractionate the medium cut into a top cut and a bottom cut, and to concentrate benzene into a separate stream;
   an Alkylation reactor/unit (A) integrated with the FCC regenerator (B) and is configured to contact the hot regenerated catalyst with the dry gas stream and a benzene stream to produce alkyl aromatics, and to continuously withdraw the hot regenerated catalyst from the FCC regenerator and send back to the FCC regenerator after alkylation reaction.

9. The system as claimed in claim 8, wherein a temperature of the alkylation reactor is in a range of 300-400° C.

10. The system as claimed in claim 8, wherein the alkylation reactor is configured to perform as a catalyst cooler or a heat sink.

* * * * *